US009284527B2

(12) United States Patent
Chuang et al.

(10) Patent No.: US 9,284,527 B2
(45) Date of Patent: *Mar. 15, 2016

(54) USE OF STEM CELL CONDITIONED MEDIUM TO INHIBIT MELANIN FORMATION FOR SKIN WHITENING

(71) Applicant: GROWGENE BIOTECH INC., Taipei (TW)

(72) Inventors: Pei-Chuan Chuang, Taipei (TW); Huei-Chun Liu, Taipei (TW)

(73) Assignee: Growgene Biotech Inc., Taipei (TW)

( * ) Notice: Subject to any disclaimer, the term of this patent is extended or adjusted under 35 U.S.C. 154(b) by 45 days.

This patent is subject to a terminal disclaimer.

(21) Appl. No.: 14/246,343

(22) Filed: Apr. 7, 2014

(65) Prior Publication Data

US 2015/0284679 A1  Oct. 8, 2015

(51) Int. Cl.
| | |
|---|---|
| *A61K 8/00* | (2006.01) |
| *A61K 8/18* | (2006.01) |
| *A61Q 5/08* | (2006.01) |
| *A61Q 19/02* | (2006.01) |
| *A61K 35/50* | (2015.01) |
| *A61K 35/12* | (2015.01) |
| *C12N 5/00* | (2006.01) |
| *A61K 8/99* | (2006.01) |

(52) U.S. Cl.
CPC ............... *C12N 5/0018* (2013.01); *A61K 8/99* (2013.01); *A61K 2800/80* (2013.01); *A61Q 19/02* (2013.01); *C12N 2501/10* (2013.01); *C12N 2502/025* (2013.01)

(58) Field of Classification Search
None
See application file for complete search history.

(56) References Cited

U.S. PATENT DOCUMENTS

| | | | | |
|---|---|---|---|---|
| 2008/0311093 | A1* | 12/2008 | Skinner | 424/93.21 |
| 2009/0136459 | A1* | 5/2009 | Wu et al. | 424/93.7 |
| 2010/0143289 | A1* | 6/2010 | Cohen et al. | 424/85.1 |
| 2010/0323027 | A1* | 12/2010 | Lim et al. | 424/520 |
| 2011/0294731 | A1* | 12/2011 | Torfi | 514/7.6 |
| 2012/0141399 | A1* | 6/2012 | You et al. | 424/62 |
| 2014/0148915 | A1* | 5/2014 | Aljitawi et al. | 623/23.72 |

FOREIGN PATENT DOCUMENTS

TW   201338810 A   10/2013

OTHER PUBLICATIONS

Arno et al. Stem Cell Research & Therapy 2014, 5:28, pp. 1-13.*
Kim, et al., "Whitening Effect of Adipose-Derived Stem Cells: A Critical Role of TGF-β1"; Biological and Pharmaceutical Bulletin; vol. 31 (2008) No. 4 p. 606-610.
Fu, Thesis Abstract for "The Potential Application of the Human Umbilical Cord Mesenchymal Stem Cells from Wharton's Jelly for Skin Wound Healing"; Abstract available as of Sep. 9, 2015 at http://handle.ncl.edu.tw/11296/ndltd/63084814835085357859; published 2010.

* cited by examiner

*Primary Examiner* — Chris R Tate
*Assistant Examiner* — Douglas F White
(74) *Attorney, Agent, or Firm* — Rosenberg, Klein & Lee

(57) ABSTRACT

A use of a stem cell conditioned medium to inhibit melanin formation for skin whitening is revealed. First, mesenchymal stem cells are cultured in a cell culture dish containing complete growth media. After mesenchymal stem cells are subcultured in a complete growth media for three times, a conditioned medium can be acquired from the basal media.

3 Claims, 4 Drawing Sheets

A

B

USE OF STEM CELL CONDITIONED MEDIUM TO INHIBIT MELANIN FORMATION FOR SKIN WHITENING

BACKGROUND OF THE INVENTION

1. Field of the Invention

The present invention relates to a use of a stem cell conditioned medium to inhibit melanin formation for skin whitening, in which the conditioned medium obtained from human Wharton's jelly-derived mesenchymal stem cells (WJMSCs) conditioned basal medium can effectively decrease tyrosinase activity and inhibit melanin formation in skin cells so as to achieve efficacy of skin whitening.

2. Description of Related Art

In mammals such as humans, skin is the soft outer covering all over a mammal body and enables to interface with the environment as the first line of defense from external factors. Therefore, skin is the most vulnerable organ to external stimuli and UV damage. In order to protect skin, melanocytes synthesize melanin to resist UV radiation. Melanin, a kind of biological pigments, is derived from tyrosine by a series of chemical reactions. In melanocytes, tyrosine is catalyzed by tyrosinase to form dihydroxyphenylalanine (Dopa), and Dopa is converted to Dopaquinone by dehydrogenation. Two other enzymes, tyrosinase-related protein 1 (TRP1) and tyrosinase-related protein 2 (TRP2) are also shown to participate in this processes to synthesize the final product of eu-melanin. Furthermore, when a skin is exposed to UV radiation, a small amounts of free radicals will be produced and thus activate signaling pathways to stimulate transcription of tyrosinase in the skin, resulting in an increased synthesis of melanin and causing the freckles formation. If people don't timely care their skin after UV radiation, increasing freckles will make the skin look dull.

Nowadays, various ingredients are identified to have whitening effects, including arbutin, acelaic acid, kojic acid, hydroquinone and the like. However, some limitations and side effects are existed, e.g. kojic acid may cause liver cancer, and hydroquinone is relatively unstable and has the potential to damage the melanocyte. Moreover, some whitening agents applied on users' skin may also cause the phenomenon of allergy, redness and discomfort. Therefore, it is necessary to develop a safer and more effective whitening ingredient.

In these years, studies of stem cells have been a growing trend in the world. Stem cells can mainly be divided into two categories, embryonic stem cells and adult stem cells. Mesenchymal stem cells (MSCs) belong to adult stem cells and have a great potential for differentiation. MSCs can differentiate into not only tissues (such as skeleton) derived from mesoderm, but also visceral cells (such as liver and pancreas) derived from endoderm and neurons derived from ectoderm. MSCs are ubiquitous in adults' bodies and can be isolated from bone marrows and various organs. However, the number of MSCs in the bodies is small, and adults' MSCs are known to gradually decrease with the age of the donors. Therefore, how to obtain a sufficient amount of MSCs becomes very important. Bone marrow MSCs are mainly derived from adult bone marrow, but invasive ways to get the bone marrow MSCs may cause pain and discomfort to donors. Umbilical cords contain a number of rich and young MSCs with strong differentiation potential, so they can be used as an important source of mesenchymal stem cells. In comparison with obtaining MSCs from bone marrows, obtaining MSCs from umbilical cords is relatively easy. Moreover, recent studies showed that adipose-derived stem cells-conditioned medium (ADSC-CM) have inhibitory effects on melanin synthesis in melanoma B16 cells (*Biol. Pharm. Bull.* 31(4) 606-610, 2008). The conditioned medium effectively achieves whitening effects by down-regulating the expression of tyrosinase and tyrosinase-related protein 1 (TRP1).

SUMMARY OF THE INVENTION

In view of the above-mentioned problems, the object of the present invention is to provide a use of a stem cell conditioned medium to inhibit melanin formation for skin whitening. The conditioned medium acquired from WJMSCs conditioned basal medium can effectively decrease tyrosinase activity and inhibit melanin formation in skin cells so as to achieve efficacy of skin whitening.

Disclosed herein is a use of a stem cell conditioned medium to inhibit melanin formation for skin whitening, wherein the stem cell conditioned medium is manufactured by the steps of (a) culturing stem cells in a cell culture dish containing a complete growth medium, wherein the complete growth medium includes α-MEM, fetal bovine serum, and human-basic fibroblast growth factors; and (b) sub-culturing the stem cells for at least three times (preferably for three times) in the complete growth medium and transferring the stem cells to a basal medium for acquiring the stem cell conditioned medium, wherein the basal medium includes α-MEM and human-basic fibroblast growth factors (without fetal bovine serum).

Disclosed herein is another use of a stem cell conditioned medium to inhibit melanin formation, wherein at least 2.5 wt. % (preferably about 2.5 wt. %-10 wt. %) of the stem cell conditioned medium is applied to a skin for decreasing tyrosinase activity and melanin synthesis.

According to an embodiment of the present invention, the stem cell is mesenchymal stem cell, preferably human Wharton's jelly-derived mesenchymal stem cell.

According to an embodiment of the present invention, the complete growth medium includes about 10 wt. %-20 wt. % of fetal bovine serum, about 2-6 ng/ml of human-basic fibroblast growth factors, and a remaining weight percentage of minimum essential medium alpha (α-MEM).

According to an embodiment of the present invention, the basal medium includes about 2-6 ng/ml of human-basic fibroblast growth factors and a remaining weight percentage of minimum essential medium alpha (α-MEM).

DETAILED DESCRIPTION OF THE PREFERRED EMBODIMENT

Figure 1A:
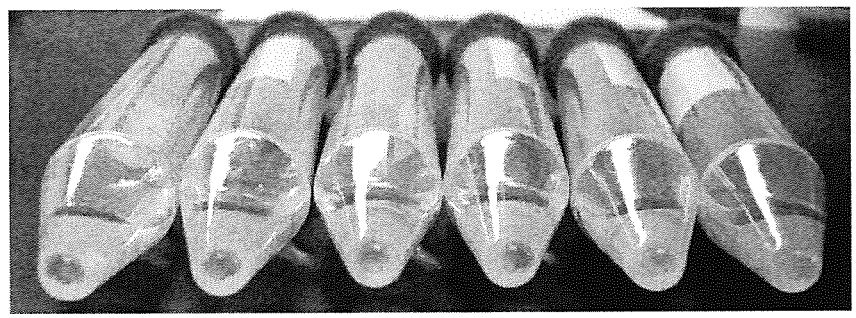
FIG. 1A is a representative diagram showing the effect of conditioned medium on melanin contents.

Disclosed herein is a use of a stem cell conditioned medium to inhibit melanin formation for skin whitening, wherein the stem cell conditioned medium is manufactured by the steps of (a) culturing stem cells in a cell culture dish containing a complete growth medium, wherein the complete growth medium includes about 10 wt. %-20 wt. % (preferably 20 wt. %) of fetal bovine serum, about 2-6 ng/ml (preferably 4 ng/ml) of human-basic fibroblast growth factors, and a remaining weight percentage of minimum essential medium alpha (α-MEM); and (b) sub-culturing the stem cells for at least three times (preferably for three times) in the complete growth medium and transferring the stem cells to a basal medium for acquiring the stem cell conditioned medium, wherein the basal medium includes about 2-6 ng/ml (preferably 4 ng/ml) of human-basic fibroblast growth factors and a remaining weight percentage of α-MEM (but without fetal bovine serum), and wherein the stem cell is mesenchymal stem cell, preferably human Wharton's jelly-derived mesenchymal stem cell.

Disclosed herein is another use of a stem cell conditioned medium to inhibit melanin formation, wherein at least 2.5 wt. % (preferably about 2.5 wt. %-10 wt. %) of the stem cell conditioned medium is applied to a skin for decreasing tyrosinase activity and melanin synthesis, wherein the stem cell conditioned medium is manufactured by the steps of (a) culturing stem cells in a cell culture dish containing a complete growth medium, wherein the complete growth medium includes α-MEM, fetal bovine serum, and human-basic fibroblast growth factors; and (b) sub-culturing the stem cells for at least three times (preferably for three times) in a basal medium for acquiring the stem cell conditioned medium, wherein the basal medium includes about 2-6 ng/ml (preferably 4 ng/ml) of human-basic fibroblast growth factors and a remaining weight percentage of α-MEM.

Hereinafter, an exemplary embodiment of the present invention will be described in detail with reference to the accompanying drawings.

Example 1

Analyze the Effect of Stem Cell Conditioned Medium on Melanin Contents

Cell Culture

Human foreskin fibroblasts (Hs68: BCRC 603800) were cultured in dishes containing complete growth medium (BD Falcon/BD biosciences) which includes Dulbecco's Modified Eagle Medium (DMEM) (Gibco) supplemented with 10% fetal bovine serum (FBS) (Gibco). Human Wharton's jelly-derived mesenchymal stem cells (WJMSC: BCRC H-WJ001) were cultured in dishes containing complete growth medium (BD Falcon/BD biosciences) which includes DMEM supplemented with 20% FBS and 4 ng/ml human-basic fibroblast growth factor (bFGF) (Peprotech). The Hs68 and the WJMSCs were incubated at 37° C. in 5% $CO_2$ and were sub-cultured after incubation for three days.

In the subculture (cell passaging) experiment, the culture medium (complete growth medium) was removed and the attached cells were rinsed by phosphate buffered saline (PBS) (Roche). After the supernatant was removed, cells were incubated in 0.05% trypsin-EDTA (Life Technologies) for 5 minutes, and then the detached cells can be acquired from the dishes. The cells were resuspended in culture medium and centrifuged at 1,200 rpm for 3 minutes. After the supernatant was removed, cell pellets were resuspended in culture medium and cultured at 37° C. in 5% $CO_2$. Then cells were sub-cultured for three times in the complete growth media.

Preparation of Conditioned Medium

Human Wharton's jelly-derived mesenchymal stem cells (WJMSCs) were seeded onto culture dishes at a cell density of $5 \times 10^4$ cells/$cm^2$ and were incubated for one day. Then the attached cells were washed three times with PBS, and the medium was replaced with basal medium (containing DMEM and 4 ng/ml bFGF). After WJMSCs were maintained for an additional 48 hours, the basal medium were collected into a 50-ml centrifuge tube and centrifuged at 2,000 rpm for 10 minutes. Then the supernatant was filtered through a 0.22 μm filtration unit (BD Falcon/BD biosciences) and used as WJMSC conditioned medium (WJMSC-CM). The WJMSC-CM was stored at −20° C.

Observation of Melanin Contents

Fibroblasts were seeded onto culture dishes at a cell density of $2 \times 10^4$ cells/$cm^2$ and were incubated for one day. Then the medium was replaced with basal medium (only containing DMEM) and WJMSC conditioned medium (0%, 2%, 5%, 10%, 50%, or 100%), and cells were maintained for an additional 48 hours. The attached cells were rinsed by phosphate buffered saline (PBS) (Roche). After the supernatant was removed, cells were incubated in 0.05% trypsin-EDTA (Life Technologies) for 5 minutes, and then the detached cells were acquired from the dishes and centrifuged at 1,200 rpm for 3 minutes. The cell pellet were further resuspended in PBS and centrifuged at 1,200 rpm for 3 minutes. The colors of cell pellets were observed and photographed.

Measurement of Melanin Contents

Melanoma B16 cells were seeded onto culture dishes at a cell density of $2 \times 10^4$ cells/$cm^2$ and were incubated for one day. Then the medium was replaced with basal medium (only containing DMEM) and WJMSC conditioned medium (0%, 2%, 5%, 10%, 50%, or 100%), and cells were maintained for an additional 48 hours. After washing with PBS, the attached cells were dissolved in 100 μl, 1N NaOH containing 50% DMSO for reaction at 60° C. for 30 minutes, and optical density at 470 nm was measured using a spectrophotometer.

Example 2

Analyze the Melanin Contents in Long-Term Treatment of Low Concentration Stem Cell Conditioned Medium Observation of Melanin Contents Fibroblasts were seeded onto culture dishes at a cell density of $2 \times 10^4$ cells/$cm^2$ and were incubated for one day. Then the medium was replaced with basal medium (only containing DMEM) and WJMSC conditioned medium (0%, 0.625%, 1.25%, 2.5%, 5%, or 10%), and cells were maintained for 7 days. The attached cells were rinsed by phosphate buffered saline (PBS) (Roche). After the supernatant was removed, cells were incubated in 0.05% trypsin-EDTA (Life Technologies) for 5 minutes, and then the detached cells were acquired from the dishes and centrifuged at 1,200 rpm for 3 minutes. The cell pellet were further resuspended in PBS and centrifuged at 1,200 rpm for 3 minutes. The colors of cell pellets were observed and photographed.

Measurement of Melanin Contents

Melanoma B16 cells were seeded onto culture dishes at a cell density of $2 \times 10^4$ cells/$cm^2$ and were incubated for one day. Then the medium was replaced with basal medium (only containing DMEM) and WJMSC conditioned medium (0%, 0.625%, 1.25%, 2.5%, 5%, or 10%), and cells were maintained for 7 days. After washing with PBS, the attached cells were dissolved in 100 μl, 1N NaOH containing 50% DMSO for reaction at 60° C. for 30 minutes, and optical density at 470 nm was measured using a spectrophotometer.

Example 3

Analyze the Effect of Stem Cell Conditioned Medium on Expression of Tyrosinase Melanoma B16 cells were seeded onto culture dishes at a cell density of $2\times10^4$ cells/cm$^2$ and were incubated in media added with basal media (only containing DMEM) and WJMSC conditioned media (0%, 5%, 10%, or 50%) for 48 hours. After washing with PBS, the attached cells were dissolved in RIPA solution (containing 50 mM Tris-HCl, pH7.4, 1% NP-40, 0.25% deoxycholic acid, 0.15 M NaCl, 1 mM EDTA, and 1 mM PMSF/NaF/sodium ortho-vanadate and protease inhibitors cocktail (Roche)). Then the cells were collected into a 1.5-ml centrifuge tube by a scraper and placed on ice for 30-60 minutes for reaction. The supernatant (cell extracts) was acquired after centrifuged at 81,200 rpm for 3 minutes. Concentration of cell extracts were detected by the Bio-Rad protein assay at an optical density of 595 nm, and 20 μg of protein was required for subsequent experiments. After boiled at 95° C. for 5 minutes, proteins were separated on an 10% SDS-polyacryamide gel by electrophoresis (SDS-PAGE), and then were transferred to polyvinyl difluoride (PVDF) membranes. PVDF membranes were immersed in a blocking solution (containing 5% skim milk and 0.1% Tween-20 in PBS) for blocking reaction at room temperature for 1 hour. Then PVDF membranes were incubated with first antibodies: anti-tyrosinase (1:1000 dilution) and β-actin (1:10000 dilution). After washed three times (each for 5 minutes) by PBST (PBS supplemented with 0.1% Tween-20), PVDF membranes were incubated with horseradish peroxidase (HRP)-conjugated secondary antibodies (Chemicon, 1:5000 dilution) for 60 minutes, and further washed three times (each for 5 minutes) by PBST. The blots were reacted with enhanced chemiluminescence (ECL, Perkin-Elmer) reagent at room temperature for 2 minutes and exposed to X-ray film. AlphaEaseFC software (Alpha Innotech Corporation) was used to protein quantification.

Results

Figure 1B:
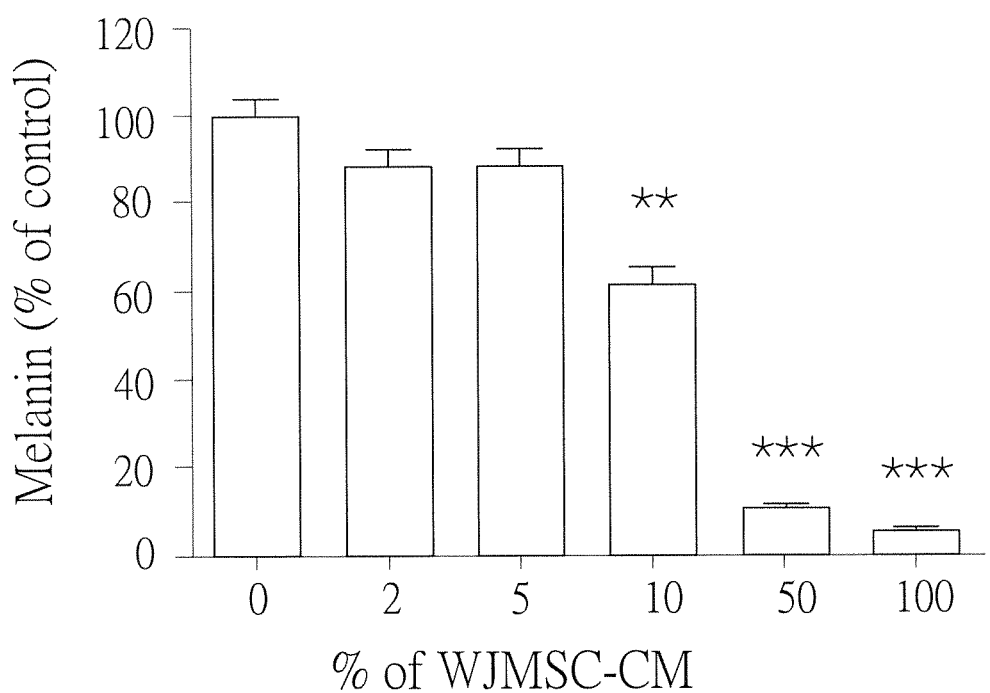
FIG. 1B is a diagram showing that WJMSC-CM effectively decreases melanin contents.

Result 1: Stem Cell Conditioned Medium can Effectively Decreases Melanin Formation Referring to FIG. 1A, it is a representative diagram showing the effect of conditioned medium (CM) on melanin contents. After a two-day incubation in a basal medium (control) or 2%-100% of stem cell conditioned medium (CM), fibroblasts (Hs68) were detached by trypsin and collected into a 15-ml centrifuge tube for observation of melanin contents. Cells treating with more than 10% of conditioned medium (CM) showed significantly decreased melanin contents. FIG. 1B is a diagram showing that WJMSC-CM effectively decreases melanin contents. The results indicated that 10% of WJMSC-CM can suppress 38.6%±5.7% of melanin contents compared with control group by student's t-test analysis. Moreover, a treatment with over 50% of WJMSC-CM can inhibit more than 90% of melanin contents. The experiments were performed in triplicate. Results were expressed as mean±SEM. P<0.01, *P<0.005. Compared to previous studies (*Biol. Pharm. Bull.* 31(4) 606-610, 2008), it is worth mentioning that only about 10% of WJMSC-CM treatment for 48 hours can effectively lower melanin contents instead of 50% of ADSC-CM. Therefore, the WJMSC-CM exhibits a better ability to inhibit melanin formation than ADSC-CM does.

Figure 2A:
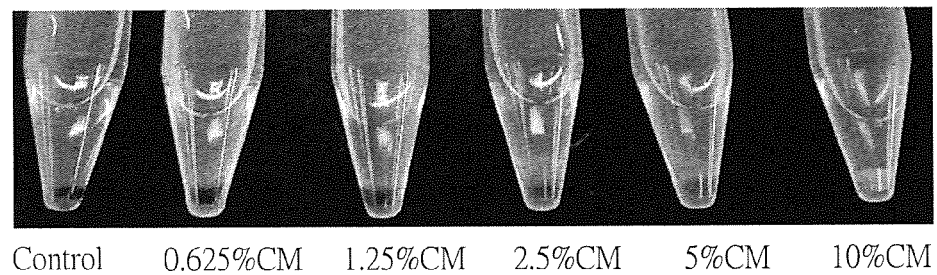
FIG. 2A is a representative diagram showing the melanin contents in long-term treatment of low concentration conditioned medium.
Figure 2B:
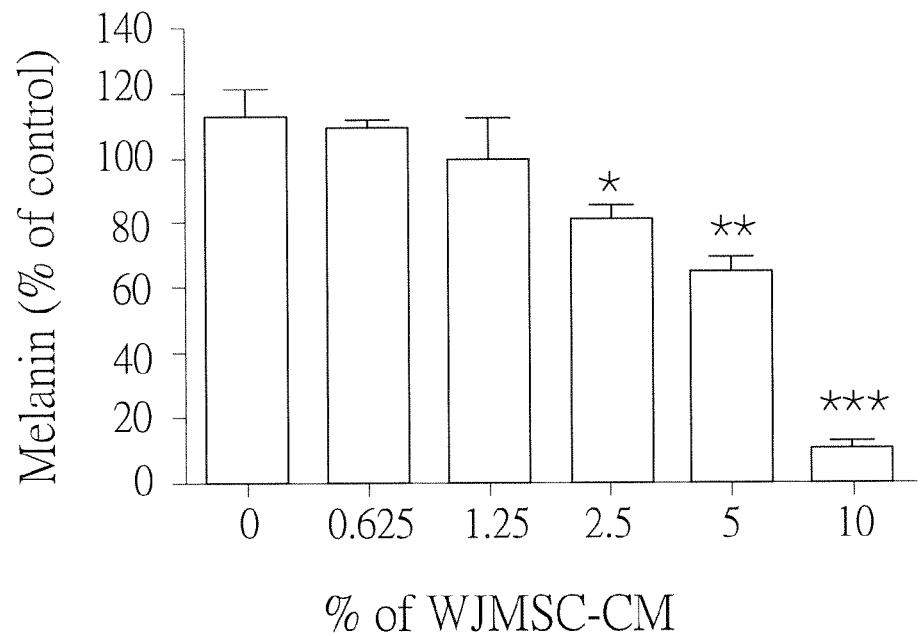
FIG. 2B is a diagram showing that long-term treatment of low concentration WJMSC-CM effectively decreases melanin contents.

Result 2: Long-Term Treatment of Low Concentration WJMSC-CM Effectively Decreases Melanin Formation Referring to FIG. 2A, it is a representative diagram showing the melanin contents in long-term treatment of low concentration conditioned medium. After a 7-day incubation in a basal medium (control) or 0.625%-10% of stem cell conditioned medium (CM), fibroblasts (Hs68) were detached by trypsin and collected into a 15-ml centrifuge tube for observation of melanin contents. The results indicated that only low concentration (more than or equal to 2.5%) of WJMSC-CM can significantly decrease melanin contents. FIG. 2B is a diagram showing that long-term treatment of low concentration WJMSC-CM effectively decreases melanin contents. By student's t-test analysis, the results indicated that 2.5%, 5% and 10% of WJMSC-CM can respectively suppress 18.2%±3.6%, 34.5%±3.9%, and 89.3%±1.8% of melanin contents. The experiments were performed in triplicate. Results were expressed as mean±SEM. *P<0.05, P<0.01, *P<0.005.

Result 3: WJMSC-CM Effectively Decreases Expression of Tyrosinase

Figure 3A:
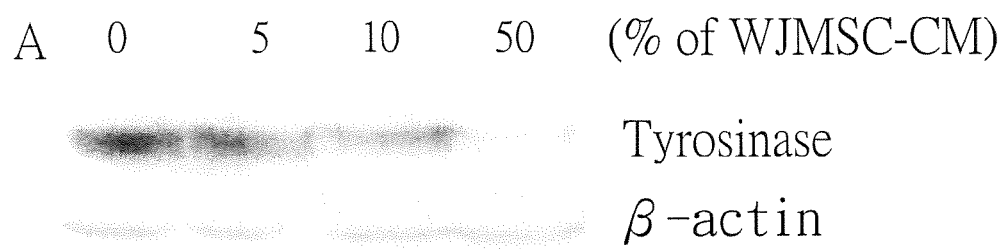
FIG. 3A is a representative diagram showing the effect of conditioned medium on expression of tyrosinase.
Figure 3B:
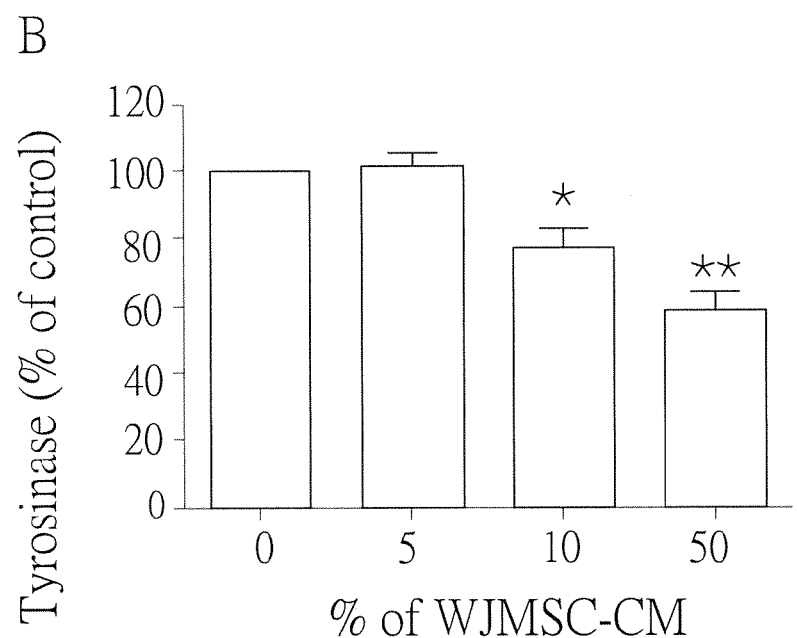
FIG. 3B is a diagram showing that WJMSC-CM effectively decreases expression of tyrosinase.

Referring to FIG. 3A, it is a representative diagram showing the effect of conditioned medium on expression of tyrosinase. After a two-day incubation in a basal medium (control) or 5%-50% of stem cell conditioned medium (WJMSC-CM), cells were detached by trypsin and collected into a 15-ml centrifuge tube for observation of tyrosinase expression in melanoma B16 cells. The results indicated that more than or equal to 10% of WJMSC-CM can significantly inhibit the expression of tyrosinase. FIG. 3B is a diagram showing that WJMSC-CM effectively decreases expression of tyrosinase. By student's t-test analysis, the results indicated that 10% and 50% of WJMSC-CM can respectively suppress 22.75%±6.0% and 40.39%±5.6% of tyrosinase expression. The experiments were performed in triplicate. Results were expressed as mean±SEM. P<0.01, *P<0.005.

Figure 4:
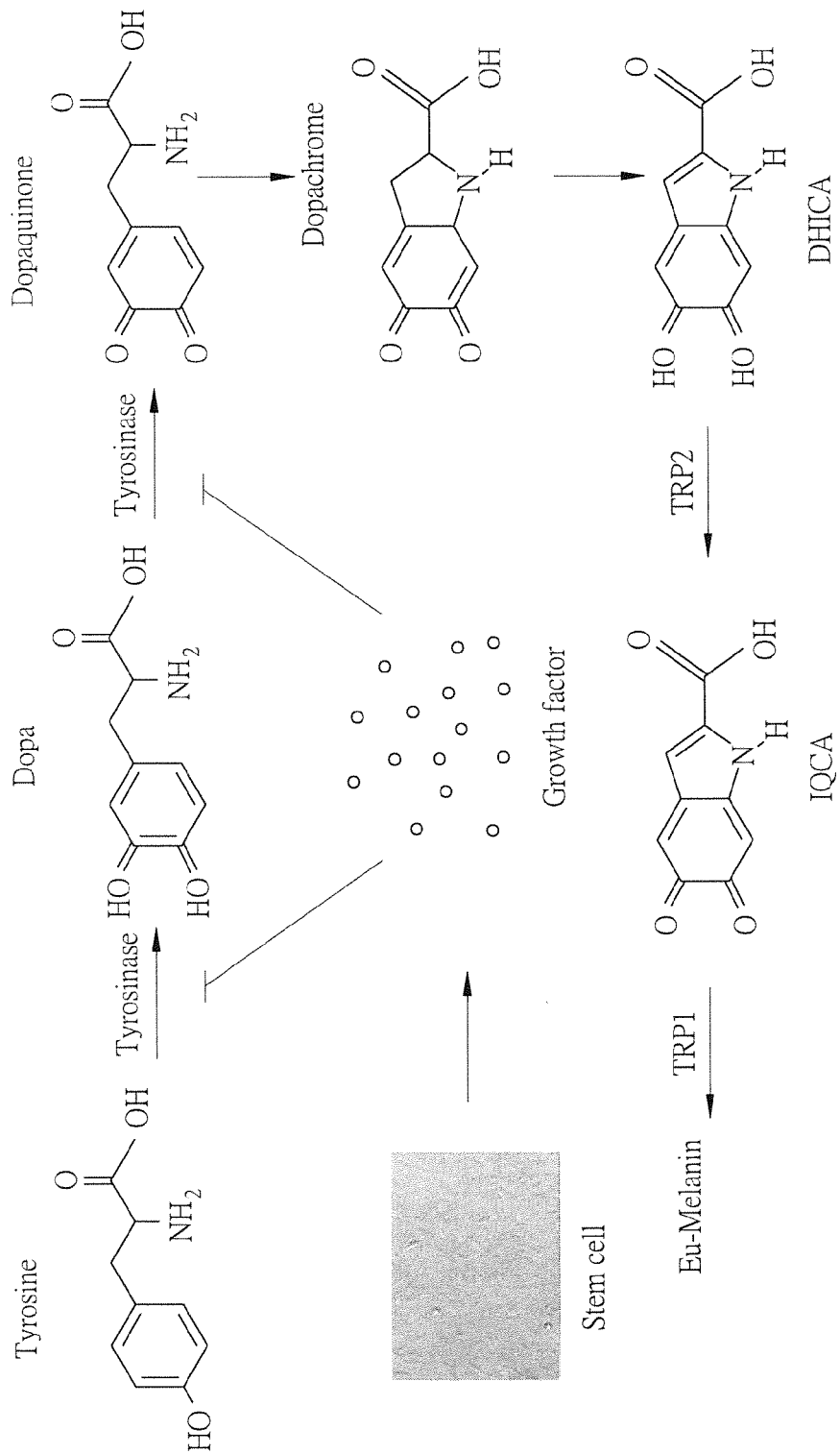
FIG. 4 is a diagram showing a whitening mechanism of WJMSC-CM according to the present invention.

To sum up, a diagram showing a whitening mechanism of WJMSC according to the present invention is revealed in FIG. 4. Human derived Wharton's Jelly mesenchymal stem cell (WJMSC) release a large number of growth factors to media, forming Wharton's Jelly mesenchymal stem cell conditioned media (WJMSC-CM). The WJMSC-CM can effectively inhibit expression of tyrosinase (the rate-limiting enzyme for controlling the production of melanin), so as to lower melanin formation. Accordingly, the WJMSC-CM can be further used as a material added to the cosmetic composition for improving users' undesired skin conditions, e.g. pigmentation and freckles formation.

According to the above description, in comparison with the traditional technique, a use of a stem cell conditioned medium to inhibit melanin formation for skin whitening according to the present invention has the advantages as following:

1. The mesenchymal stem cell conditioned medium (WJMSC-CM) containing a large number of growth factors can effectively decrease melanin synthesis by inhibiting tyrosinase expression, so as to solve the problems of pigmentation and freckles formation in skin.
2. In a short-term (48 hours) treatment experiment, 50% of adipose-derived stem cells-conditioned medium (ADSC-CM) is required for inhibiting melanin synthesis significantly, whereas only about 10% of WJMSC-CM can achieve the same effect. Therefore, the WJMSC-CM has a better ability to inhibit melanin production than ADSC-CM does.
3. Only treating cells with low concentration (about 2.5%-10%) WJMSC-CM for 7 days can effectively achieve efficacy of suppressing melanin synthesis. Therefore, the WJMSC-CM can be further used as an ingredient of whitening agents.

4. In comparison with obtaining MSCs from bone marrows, Wharton's jelly MSCs can be acquired from newborn babies' unwanted umbilical cords. Therefore, collecting MSCs from umbilical cords may not cause pain to donors and can prevent ethical problems. Moreover, the number of stem cells in umbilical cords is larger than that of other parts in human's bodies, so obtaining MSCs from umbilical cords is relatively easy.

5. In comparison with bone marrows-derived MSCs, Wharton's jelly MSCs belong to the earlier stage cells and can differentiate into much more cell types. Therefore, the conditioned media of Wharton's jelly MSCs, which contains protein factors, have a better ability to suppress melanin synthesis for skin whitening.

What is claimed is:

1. A method of whitening skin using a stem cell conditioned medium, comprising:
applying at least 2.5 wt. % of the stem cell conditioned medium to the skin of a subject in need thereof so as to decrease tyrosinase activity and melanin synthesis thereby whitening the skin; and wherein said stem cell conditioned medium is produced by (a) culturing human Wharton's jelly mesenchymal stem cells in a cell culture dish containing a complete growth medium, wherein the complete growth medium includes α-MEM, fetal bovine serum, and human-basic fibroblast growth factors; and (b) sub-culturing the Wharton's jelly mesenchymal stem cells in the complete growth medium and transferring the stem cells to a basal medium to obtain said stem cell conditioned medium, wherein the basal medium includes α-MEM and human-basic fibroblast growth factors.

2. The method of claim 1, wherein the complete growth medium includes about 10 wt. %-20 wt. % of fetal bovine serum, about 2-6 ng/ml of human-basic fibroblast growth factors, and a remaining weight percentage of α-MEM, and the basal medium include about 2-6 ng/ml of human-basic fibroblast growth factors and a remaining weight percentage of α-MEM.

3. The method of claim 1, wherein about 2.5 wt. %-10 wt. % of the stem cell conditioned medium is applied to the skin.

* * * * *